United States Patent
Chen et al.

(10) Patent No.: US 6,708,559 B2
(45) Date of Patent: Mar. 23, 2004

(54) DIRECT, NON-DESTRUCTIVE MEASUREMENT OF RECESS DEPTH IN A WAFER

(75) Inventors: Linda X. Chen, Wappingers Falls, NY (US); Larry Varnerin, Pleasant Valley, NY (US)

(73) Assignee: Infineon Technologies AG, Munich (DE)

( * ) Notice: Subject to any disclaimer, the term of this patent is extended or adjusted under 35 U.S.C. 154(b) by 225 days.

(21) Appl. No.: 09/965,093

(22) Filed: Sep. 28, 2001

(65) Prior Publication Data

US 2003/0061890 A1 Apr. 3, 2003

(51) Int. Cl.⁷ .............................................. G01F 17/00
(52) U.S. Cl. ....................................................... 73/149
(58) Field of Search ........................ 73/104, 105, 149, 73/866; 33/1 V

(56) References Cited

U.S. PATENT DOCUMENTS

| | | | |
|---|---|---|---|
| 4,628,728 A | * 12/1986 | Taylor et al. ................. | 73/149 |
| 4,840,487 A | 6/1989 | Noguchi et al. ............ | 356/355 |
| 5,242,831 A | * 9/1993 | Oki ............................. | 73/104 |
| 5,691,540 A | 11/1997 | Halle et al. .................. | 250/372 |
| 6,124,141 A | 9/2000 | Muller et al. ................ | 257/529 |
| 6,275,297 B1 | 8/2001 | Zalicki ........................ | 356/496 |
| 6,306,545 B1 | * 10/2001 | Carlson et al. | |

* cited by examiner

Primary Examiner—Robert Raevis

(57) ABSTRACT

A direct and non-destructive method for measuring recess depth in a semiconductor wafer through use of a solvent, comprising:
 a) placing a recessed wafer into a track;
 b) pouring a solvent into the wafer;
 c) commencement of spinning the track-wafer-solvent to recess the solvent into the wafer trench solvent;
 d) subjecting the track-wafer-solvent from step c) to a subsequent spinning step to spin-off any remaining solvent on the surface of the wafer to leave the wafer trench filled with solvent;
 e) weighing the solvent-filled-trench wafer;
 f) subjecting the solvent-filled-trench wafer to heating to remove the solvent; and
weighing the solvent-free wafer to determine the difference in weight, and using the density of the solvent together with the difference in weight to determine the recess depth.

20 Claims, 2 Drawing Sheets

WAFER AFTER RESIST
RECESS AND ETCHING

PUT INTO TRACK
APPLY SOLVENT

SPINNING

SPINNING

PUT INTO BALANCE
AND WEIGHT OBTAIN
WEIGHT W2

PUT INTO BALANCE AND
WEIGHT OBTAIN WEIGHT W1
BAKE, REMOVE SOLVENT

DIRECT, NON-DESTRUCTIVE MEASUREMENT OF RECESS DEPTH IN A WAFER

BACKGROUND OF THE INVENTION

1. Field of the Invention

The present invention relates to an effective, simple, direct and non-destructive method to measure recess depth in a wafer by putting the wafer into a track where a solvent is poured, commencement of spinning the wafer in the track to fill-up the recess, and subsequent spinning-off of the remaining solvent so that no solvent remains on the wafer surface, weighing the wafer, heating to remove the solvent, and again weighing to ascertain the difference in weight or the amount of solvent imbibed by the trenches together with solvent density, to permit a simple calculation of the recess depth.

2. Description of the Prior Art

In the ASG and LOCOS resist or polysilicon recess process, control of the recess depth is crucial as the recess depth determines both parasitic leakage and the capacity of the transistor, thus controlling the storage time of the transistor.

At present, profiling techniques such as those performed with SEMs or AFM are used to monitor the recess depth within round or elliptical depths in a chip.

However, SEM measurements are time-consuming, costly and destructive. On the other hand, AFM measurements of recess depths in a trench is done in the kerf, in which the trench size is large enough to accommodate the bulky AMF tip. Because the recess depth is closely related to the size of the trench, a correlation needs to be established between the large trench on the kerf and the real trench in the arrays.

U.S. Pat. No. 6,275,297 discloses methods of and apparatus for measuring the depth of structures on a semiconductor substrate. The measurement is accomplished by a broadband light source that irradiates the recessed and non-recessed portions. A detector detects reflected light including a first spectral component comprising light reflected from the recessed portions and a second spectral component comprising light reflected from the non-recessed portions, wherein at least one of the first and second components further comprises a third component comprising light reflected from the dielectric layer. Spectral reflectance information of the detected rays is stored and a plot of reflectance intensity versus wavelength is generated. Depth geometries of the recesses and the dielectric layer are determined relative to the at least one reference interface based on an interferometric analysis of the plot.

An assembly for measuring a trench depth parameter in a work-piece is disclosed in U.S. Pat. No. 5,691,540. The assembly comprises an ultra-violet radiation source; a split fiber bundle having a first branch for propagating the ultra-violet radiation from the radiation source to a lens, and a second branch; a lens for focusing the UV radiation to the workpiece and refocusing an ultra-violet interference signal to the second branch; and a detector responsive to the ultra-violet interference signal received through the second branch. The detector transforms the ultra-violet interference signal to an electrical signal which is a measure of a trench depth of the workpiece. The ultra-violet interference signal is developed when ultra-violet radiation propagates through the workpiece and reflects from its base region to thereby interfere with ultra-violet radiation that is directly reflected by a workpiece surface which is different from the base region.

U.S. Pat. No. 6,124,141 discloses a non-destructive method for measuring the depth at which the top surface of a buried interface is located in a semiconductor substrate. The method employs a Fourier Transform Infrared measurement, and comprises subjecting the semiconductor substrate containing the buried interface to a beam of infrared light and then detecting and analyzing the spectrum of a return signal by a Fourier analysis. The spectrum as analyzed by the Fourier analysis is then compared to calibration spectra to thereby determine the depth of the top surface of the buried interface. The invention also uses a device for determining the depth of a buried interface below the surface of a semiconductor substrate. That device comprises a FTIR spectrophotometer which illuminates the substrate with a source of infrared radiation and which produces a Fourier transform of a return signal reflected from the substrate. The device includes a library of stored calibration spectra, along with means for comparing the Fourier transform return signal to the calibration spectra to determine the depth of the buried interface.

U.S. Pat. No. 4,840,487 discloses an apparatus for measuring etching pits by employing a light source having a small absorptivity with respect to a groove or pit as an object of irradiation to insure a satisfactory change in the interference intensity of the detracted light which is reflected from the object. The apparatus includes a detector means provided with the freedom of movement in two axial directions which are perpendicular to each other and in the direction of rotation. In addition, as a laser source, a He—Cd, $N_2$ or Ar laser may be employed in addition to a He—Ne laser to detect changes in their interference intensities, and the etch depth is calculated on the basis of the detected changes.

There is a need in the art of measuring recess depth in the wafer for an effective, simple, direct and non-destructive measurement technique for recess process control, especially with device dimensions of groundrule shrinkage to 0.13 microns and below, as the current profiling techniques are becoming increasingly more costly and difficult to correlate.

SUMMARY OF THE INVENTION

One object of the present invention is to provide an effective and non-destructive measurement technique for recess process control or depth measurement in a semiconductor chip, where the device dimensions or ground rules have shrunk to 0.13 microns and below.

Another object of the present invention is to provide a simple, non-destructive measurement technique for recess process control or depth where the device dimension or groundrules have shrunk to 0.13 microns and below without employing SEM or AMF profiling techniques.

A further object of the present invention is to provide a direct, non-destructive measurement technique for recess process control or depth measurement in a semiconductor, where device dimension or ground rules have shrunk to 0.13 microns and below, that are less costly and less difficult to correlate.

In general, the effective, simple, direct and non-destructive method for measuring recess depth in a semiconductor chip of the invention is through the use of a solvent, and entails:

placing the recessed wafer into a track where a solvent is poured onto the wafer and commencing spinning of the wafer to recess the solvent into the trench and fill it up;

subsequently spinning off the remaining solvent so that no solvent remains on the surface of the wafer;

weighing the wafer;

heating to remove the solvent;

again weighing to ascertain the difference in the two weights or the amount of the solvent imbibed by the trenches; and calculating recess depth premised around the density of the solvent and the weight difference.

DETAILED DESCRIPTION OF PREFERRED EMBODIMENT OF THE INVENTION

Figure 1:
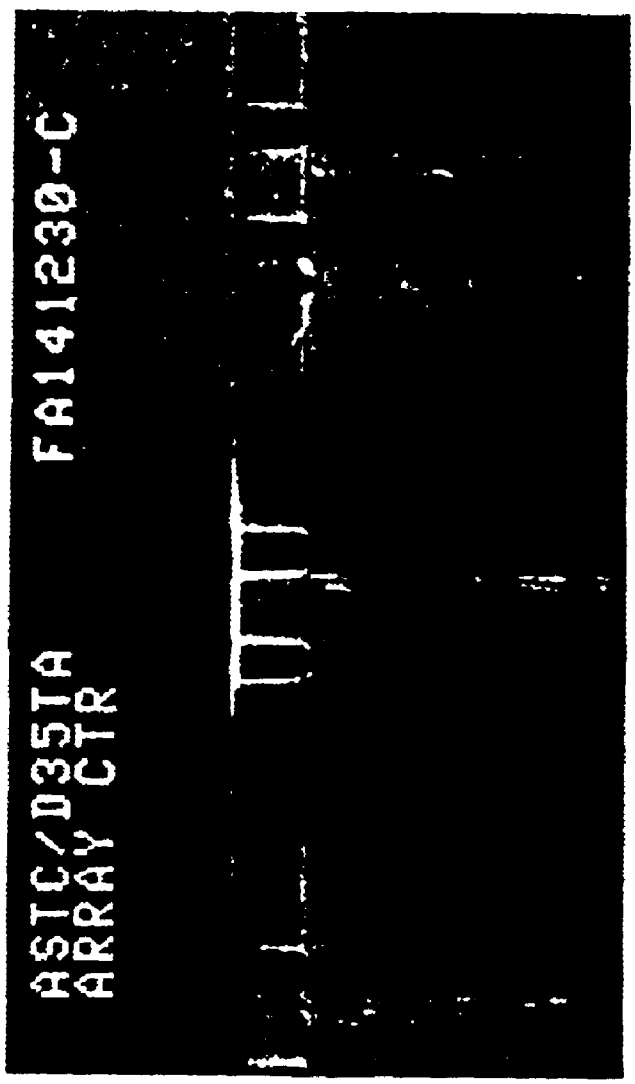
FIG. 1 is a Scanning Electron Micrograph of a typical wafer profile after resist recess and etching.

Reference is now made to FIG. 1 which shows scanning electron micrographs (SEMs) of a typical wafer profile after resist recess and etching. The recess material Accuflow 913 EL from Honeywell. The POR resist recess etch recipe was applied to the wafer. From x-section pictures of the array center, and array edge, the most important data is collected; namely, the recess depth. In addition to the recess depth, information regarding the maximum variation is also collected, that is, the maximum variation within the wafer is 0.22 microns, within the array centers 0.11 micron and from the array center to the edge 0.14 microns or smaller.

For a 110 nm DRAM product, there is a 308 chips per 8 inches of wafer, and a half billion trenches per chip. Assuming that each trench has a width of 1.25 nm, a length of 220 nm, and a depth of 1.3 microns, the total volume of trench that would have potential to be filled by a solvent is approximately 4.3 $mm^3$. The particular solvent utilized has a density or specific gravity of about 1.4 $g/cm^3$, and the weight difference is about 6 mg. The balance scale utilized is easily capable of weighing up to 100 g with a resolution of up to 0.05 mg. This corresponds to less than 1% noise level; in other words, easy measurement of a trench with recess depth of 1.3 microns can be made with an accuracy of up to 13 nm.

FIG. 2 is a schematic of the invention process for measuring the recess depth of a semiconductor chip. After recess, the wafers are put into a track where several mil of a solvent with a density of 1.4 g/cm3 is poured into the wafers, whereupon spinning is started. Because of the capillary force between the surface of the trenches and the solvent, the solvent easily recesses into the trench and fills it up. A subsequent spinning step is used to spin off the remaining solvent and render a wafer with trench filled with the solvent. However, at this juncture no solvent remains on the surface of the wafer. The wafer is weighted by a balance and then placed into a hot plate to remove the solvent by evaporation, whereupon the wafer is weighed again. The difference of the weight is the weight of the solvent imbibed by the trenches.

Figure 2A:
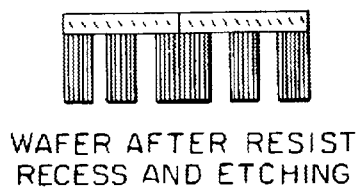
FIGS. 2a–2e (collectively FIG. 2) are schematics of the non-destructive method of measuring recess depth of a wafer utilizing a solvent in accordance with the invention process.
Figure 2B:
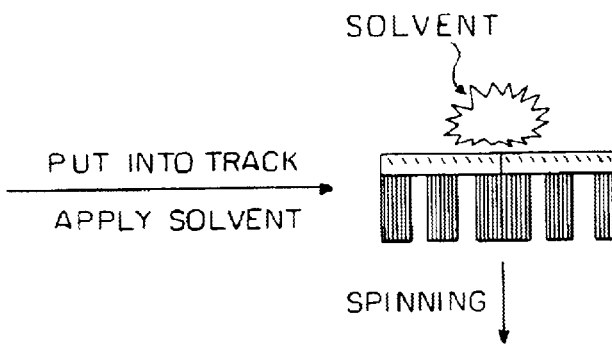

FIGS. 2a to 2b depicts a wafer after it is put into a track and solvent is first applied, followed by commencement of spinning.

Figure 2C:

FIG. 2c depicts the wafer filled with the solvent.

Figure 2D:
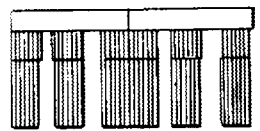

FIG. 2d depicts the wafer after the second spinning process.

Figure 2E:
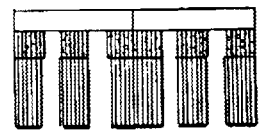

FIG. 2e depicts the wafer after it is put into a balance and weighted following removal of the solvent by heating to obtain weight W2.

The following calculations will show the amount the solvent that can be imbibed by 8 inches of wafer in the invention process:

The volume of one DT trench is $$1.3 \; um*Pi*125/2 \; nm*220/2 \; nm = 2.8 \; 10^{-11} \; mm^3$$

The number of DT per wafer is $308 \times 0.5 \times 10^9 = 1.54 \times 10^{11}$ The total volume of DT trenches per wafer is $2.8 \times 10^{-11} \; mm^3 \times 1.54 \times 10^{11} = 4.3 \; mm^3$ Assume the density of solvent is 1.4 $g/cm^3$, the weight of the solvent that can be imbibed by trenches=4.3 $mm^3 \times 1.4$ $g/cm^3 = 6.0$ mg The balance used can easily measure a 100 g object with resolution up to 0.05 mg.

The invention method takes advantage of capillary force between the surface of the trenches and the chosen solvent. Capillary force is the reaction between contacting surfaces of a liquid and a solid that distorts the liquid surface from a planar shape; it works very effectively in the size range of 1–100 microns.

The invention method is not limited to 110 nm DRAM products or recess processes. The method is applicable to any process wherein there is a need to monitor the depth of huge numbers of trenches with relatively uniform depth across the wafers.

We claim:

1. A method for measuring recess depth in a semiconductor wafer through use of a solvent, comprising:
    a) placing a recessed wafer into a track;
    b) pouring a solvent into the wafer;
    c) commencement of spinning the track-wafer-solvent to recess said solvent into the wafer trench solvent;
    d) subjecting the track-wafer-solvent from step c) to a subsequent spinning step to spin-off any remaining solvent on the surface of said wafer to leave the wafer trench filled with solvent;
    e) weighing the solvent-filled-trench wafer;
    f) subjecting the solvent-filled-trench wafer to heating to remove said solvent; and
    g) weighing the solvent-free water to determine the difference in weight, and using the density of the solvent together with the difference in weight to determine the recess depth.

2. The method of claim 1 wherein said solvent is an organic solvent.

3. The method of claim 2 wherein said solvent is characterized by a density of about 1.4 $g/cm^3$.

4. The method of claim 3 wherein said semiconductor wafer has a device dimension of 0.13 $\mu$m or less.

5. The method of claim 1 wherein said semiconductor wafer includes 308 chips per 8 inches of a wafer, and a half billion trenches per chip, each chip being a 110 nm DRAM product.

6. The method of claim 5 wherein each trench has a width of 125 nm, a length of 220 nm and a depth of 1.3 $\mu$m.

7. The method of claim 6 wherein the total volume of trench filled-up with said solvent is about 4.3 $mm^3$.

8. The method of claim 7 wherein said weight difference is about 6 mg.

9. The method of claim 1 wherein said recess is a polysilicon recess.

10. The method of claim 9 wherein said polysilicon recess results from an ASG or a LOCOS process.

11. A method of measuring recess depth in a semiconductor wafer, the method comprising:
   providing a wafer including a plurality of recesses, the wafer having a device dimension of 0.13 μm or less;
   filling each of the recesses with a liquid;
   determining a weight of the wafer with the liquid in each of the recesses;
   determining a weight of the wafer with no liquid in any of the recesses; and
   determining in a recess depth for each of the recesses based upon a difference in the weight with the liquid and the weight with no liquid.

12. The method of claim 11 wherein the wafer is placed in a track prior to filling each of the recesses with a liquid.

13. The method of claim 11 wherein filling each of the recesses with a liquid comprises pouring a liquid onto the wafer and subsequently spinning the wafer.

14. The method of claim 13 wherein spinning the wafer comprises performing an initial spinning step to cause the liquid to enter each of the recesses followed by a subsequent spinning step to remove remaining solvent from a surface of the wafer.

15. The method of claim 11 and further comprising heating the wafer to remove liquid from the recesses.

16. The method of claim 15 wherein the heating step is performed before determining a weight of the wafer with no liquid in any of the recesses.

17. The method of claim 11 wherein the liquid comprises an organic solvent.

18. The method of claim 11 wherein the liquid is characterized by a density of about 1.4 g/cm$^3$.

19. The method of claim 11 wherein said semiconductor wafer has a device dimension of 0.13 μm or less.

20. The method of claim 11 wherein said semiconductor wafer comprises a DRAM product.

\* \* \* \* \*